United States Patent [19]

Zeitlin et al.

[11] 4,278,503
[45] Jul. 14, 1981

[54] LOW BROMINE CONTENT GLACIAL ACETIC ACID

[75] Inventors: Martin A. Zeitlin; Jon J. Harper, both of Naperville, Ill.

[73] Assignee: Standard Oil Company (Indiana), Chicago, Ill.

[21] Appl. No.: 106,669

[22] Filed: Dec. 26, 1979

[51] Int. Cl.³ .................... B01D 3/14; C07C 51/44; C07C 51/16
[52] U.S. Cl. .................................. 203/28; 203/48; 203/39; 62/542; 562/549; 562/608
[58] Field of Search .............. 562/608, 549; 260/707; 62/542, 541; 203/28, 48, 81, 91, 39, 99, DIG. 19

[56] References Cited

U.S. PATENT DOCUMENTS

| | | | |
|---|---|---|---|
| RE. 23,810 | 3/1954 | Schmidt | 62/543 |
| 2,823,242 | 2/1958 | McKay | 62/544 |
| 2,884,451 | 4/1959 | Graham | 562/608 |
| 3,293,292 | 12/1966 | Olivier et al. | 560/231 |
| 3,350,445 | 10/1967 | Binniag et al. | 562/608 |
| 3,561,225 | 2/1971 | Hinton | 62/541 |
| 3,578,706 | 5/1971 | List et al. | 562/414 |
| 3,616,268 | 10/1971 | Phillou | 62/541 |
| 4,111,986 | 9/1978 | Zimmerschied | 560/241 |

*Primary Examiner*—Wilbur L. Bascomb, Jr.
*Attorney, Agent, or Firm*—Fred R. Ahlers; William T. McClain; William H. Magidson

[57] ABSTRACT

Excessive energy consumption of a combination of multi-fractionations and multi-distillations of concentrating aqueous acetic acid product of liquid phase oxidations, especially oxidation of liquid n-butane with oxygen gas while the butane is dissolved in liquid acetic acid containing a catalyst system comprising Co-Br or Co-Mn-Br, is avoided and an otherwise hard to remove bromo-ketone is readily removed by a combination of sequential steps of decompressing the oxidation reaction mixture to remove unreacted butane as well as gaseous products, heat treating the decompressed liquid at a temperature of from 150° C. up to 200° C. for from 15 up to 150 minutes, subjecting the heat treated liquid to fractionation while recycling to the rectification zone thereof an aqueous portion of low boiling impurities as a means for concentrating the acetic acid and thereafter further concentrating the acetic acid produced by continuous fractional crystallization.

3 Claims, No Drawings

LOW BROMINE CONTENT GLACIAL ACETIC ACID

FIELD OF INVENTION

This invention relates to the preparation of glacial acetic acid from n-butane and more specifically pertains to the preparation of glacial acetic acid from the liquid reaction effluent or its debutanized liquid fraction obtained by liquid n-butane oxidation with oxygen gas at a temperature of from 120° C. up to 235° C. in the presence of an acetic acid solution containing the system of catalysis comprising bromide ions in combination with ions of cobalt or cobalt and manganese by decreasing the bromine content of the reaction effluent or said liquid fraction thereof by a step of continuous fractional crystallization and a step of heat treating at a temperature of from 150° C. up to 200° C. for from 15 minutes up to 150 minutes before or after the distillative removal of organic impurities boiling lower than acetic acid and separation of acetic acid from organic materials boiling higher than acetic acid including cobalt or cobalt and manganese salts of organic acids.

STATE OF THE ART

Acetic acid at high selectivity can be produced at high conversion of n-butane by its oxidation as a liquid with oxygen gas at a temperature in the range of from 120° C. up to 235° C. and a gauge pressure of from 35 up to 210 kg/cm$^2$ in the presence of an acetic acid solution containing bromide ions in combination with ions of one or more transition metals as components of catalysis. According to U.S. Pat. No. 3,293,292 it is essential to use both cobalt and manganese as the transition metal component of said catalysis.

However, according to the later U.S. Pat. No. 4,111,986 the same high conversion of n-butane at high selectivity to acetic acid can be accomplished using cobalt as the sole transition metal component of said catalysis provided that for each gram mole of n-butane to be so oxidized there are employed from 1.0 up to 50 milligram equivalents of cobalt and from 2 to 50 milligram equivalents of bromine as components of the needed catalysis.

Said oxidations of n-butane produce acetate esters and ketones boiling at temperatures below the boiling point temperature of acetic acid as well as the higher carbon atom content aliphatic mono-carboxylic acids propionic and butyric acid which have boiling temperatures above the boiling temperature of acetic acid, such acetate esters, ketones and higher aliphatic acids as products are produced in impurity level amounts and can be removed by simple distillation from the debutanized (removal of unreacted n-butane) liquid reaction effluent. Such debutanized reaction effluent contains mainly acetic acid (65 to 80 weight percent) and water (20 to 30 weight percent). However, there is one co-product produced as a result of the bromide ion component of catalysis which is difficult to remove to the impurity level which can be tolerated in acetic acid used as reactant and/or reaction solvent. It is appreciated that for some uses of acetic acid (glacial) as reactant and/or reaction solvent, that only substantially zero bromine content is acceptable but is not specified in commercial specifications.

Said difficultly removable impurity co-product has now been found to be 3-bromo-2-butanone. Its boiling temperature and that of acetic acid and of acetic acid-water compositions formed during fractionation are so close that to effect separation of said bromoketone by fractionation would require an inordinately large number of theoretical separation (tray or packed) units not acceptable for commercial operation.

Techniques have been proposed for decreasing the bromine content of acetic acid. It is not apparent from the description of such techniques that they are directed to decreasing the 3-bromo-2-butanone content of acetic acid even though there is mention of converting the bromine in organic (coordinate bound) bromides to inorganic (ionic) bromides.

According to U.S. Pat. No. 3,578,706 bromine is removed from bromine contaminated acetic acid by stirring such contaminated acetic acid at elevated temperatures (30° to 118° C.) in the presence of a finely divided metal having an electrochemical potential between magnesium and iron, or the oxides, hydroxides or salts of such metals and then subjecting the acetic acid so treated to ion exchange. The treatment with the metal converts organic bromides to inorganic bromides.

It might be thought that the catalytic hydrogenation technique of U.S. Pat. No. 2,884,451 for removal of odorous substances and materials of a reducing nature from acetic acid obtained by the non-catalytic oxidation of $C_4$ to $C_8$ paraffinic hydrocarbons might also convert organic bromide impurities to easily removable inorganic bromides. However, it has been found in our laboratories that such catalytic hydrogenation of the liquid phase of the organic bromide contaminated acetic acid does not suitably decrease the organic bromide contamination.

It has also been found in our laboratories that treatment of the organic bromide contaminated acetic acid with an alkali metal hydroxide, bicarbonate or carbonate and then distilling the treated acid or that treatment of the organic bromide contaminated acetic acid with a solid absorbant does not suitably decrease the organic bromide contamination. Rather it has been found that more severe treatment is necessary. For example, the organic bromide contamination can be suitably decreased by first contacting a vapor phase of the organic bromide contaminated acetic acid with hydrogen and a hydrogeation catalyst (e.g. metallic platinum or palladium per se or disposed on the surface of activated carbon) and then either (1) contacting the vapors with a bed of solid absorbant (e.g. alumina or activated carbon), or (2) condensing the treated acetic acid vapors and treating the liquid state of acetic acid with an alkali metal hydroxide, carbonate or bicarbonate followed by distillative recovery of acetic acid. Such combinations of vapor phase catalytic hydrogenation of organic bromide contaminated acetic acid with solids are the subject matter of claims in the copending U.S. patent application Ser. No. 970,226, now U.S. Pat. No. 4,228,307 and Ser. No. 970,222, now U.S. Pat. No. 4,227,971, both filed on Dec. 18, 1978.

It has now been discovered that the 3-bromo-2-butanone contamination of glacial acetic acid can be substantially decreased by the use of a heat treating step and a cryogenic fractional crystallization step before the removal of the last amounts of water from the acetic acid, that is, before the last step of forming glacial acetic acid.

STATEMENT OF THE INVENTION

The present inventive technique to decrease the 3-bromo-2-butanone contamination of a useful acetic acid produced from an acetic acid product obtained from the oxidation of liquid n-butane with oxygen gas at a temperature of from 120° C. up to 235° C. in the presence of an acetic acid solution of a bromine liberating compound and a cobalt salt or a cobalt and manganese salt providing bromide ions in combination of ions of cobalt or of cobalt and manganese introduces a thermal step of converting 3-bromo-2-butanone to 1-butene-3-one and inorganic bromide or bromides, and a cryogenic step of concentrating the aqueous acid mixture and rejecting 3-bromo-2-butanone into the recovery of acetic acid which includes the steps of debutanizing the liquid reaction effluent by decreasing its pressure (decompressing) to a gauge pressure of from 22 down to 0 kg/cm$^2$, removing by distillation organic compounds (esters and ketones) boiling lower than acetic acid and then an acetic acid fraction containing from 5% to 10% water and $C_1$ to $C_4$ aliphatic acid homologues of acetic acid (formic, propionic and butyric acids) leaving a residue containing co-products boiling higher than acetic acid and catalyst metal salts of organic acids (mainly acetates), and dehydrating the aqueous acetic acid fraction.

The 3-bromo-2-butanone decreasing effects of the thermal conversion step and the cryogenic step depend on the co-presence of water with acetic acid. The thermal conversion is believed to involve the reaction of water with 3-bromo-2-butanone to produce 1-butene-3-one and one or more inorganic bromides, probably catalyst metal bromides. The cryogenic step is a continuous fractional crystallization which rejects organic impurities not by precipitation in a crystalline form, but rather as a solute in an acetic acid-water mother liquor of higher water content than the acetic acid-water crystalline product frozen out of the feed to the cryogenic step.

Each of said steps can operate effectively on the debutanized liquid portion of the liquid reaction effluent. For example, continuous fractional crystallization practiced on the liquid debutanized fraction containing 66.4 wt.% acetic acid, 24.85 wt.% water and 0.72 wt.% 3-bromo-2-butanone, on a once through basis, can produce a product containing 78.7 wt.% acetic acid, 18.73 wt.% water and 0.06 wt.% 3-bromo-2-butanone and a waste liquor containing 60.6 wt.% acetic acid, 30.1 wt.% water and 0.77 weight percent 3-bromo-2-butanone. Thus a product containing 3-bromo-2-butanone of only 8.33% of that in the feed (a 91.66% decrease) is achieved by the cryogenic process.

The thermal conversion step is carried out at temperatures of from 150° C. up to 200° C. for from 15 minutes up to 150 minutes while some water is still present for its aforementioned reaction with 3-bromo-2-butanone to produce 1-butene-3-one and one or more inorganic bromides. There is substantial evidence that a substantial proportion of the inorganic bromide formed is catalyst metal bromide (e.g., by reaction of catalyst metal acetate with HBr) because additionally formed inorganic bromide appears in the bottom fraction of distillation as does the catalyst metal acetate.

More specifically, a total liquid effluent from the oxidation of n-butane with oxygen gas according to the processes before described has an inorganic bromide content of 0.2122 weight percent and a 3-bromo-2-butanone content of 0.765 weight percent. Maintaining such effluent at a temperature of 150° C. for 80 minutes decreased the bromoketone content to 0.019 weight percent and increased the inorganic bromides to 0.72 weight percent. But maintaining said liquid effluent at a temperature of 200° C. for 40 minutes or 80 minutes decreased the bromoketone content to 0.016 weight percent and to a not detectable level, respectively, while increasing the inorganic bromides to the respective levels of 0.68 and 0.736 weight percent. After such heat treatment and upon debutanizing the liquid reaction effluents and distilling them to recover a product fraction (85 to 90% of the charge to distillation), a product fraction containing less than 0.01 weight percent 3-bromo-2-butanone can be recovered. The foregoing indicates that the thermal debromination of 3-bromo-2-butanone is effective even at pressures well above atmospheric pressure and prior to debutanization of the liquid reaction effluent.

The best mode presently contemplated for the practice of the present invention comprises decompressing the liquid reaction effluent from 56 to 63 kg/cm$^2$ gauge pressure and 176°–177° C. down to a gauge pressure of from 15 down to 2.5 kg/cm$^2$ and a temperature of from 176°–177° C. while maintaining the remainder of the effluent at a temperature between 118° C. and 177° C. which causes at least 80 weight percent of the unreacted butane to be removed in a mixture which comprises from 14 up to 32 weight percent of the liquid reaction effluent before being decompressed.

The effectiveness of such preferred conditions for decompressing and debutanizing the liquid reaction effluent can be demonstrated by data from such operations on liquid reaction effluent having the composition shown in TABLE I to follow which effluent is prepared by the oxidation of n-butane with oxygen gas at a temperature of 182° C., a gauge pressure of 63.6 kg.cm$^2$, a residence time of 41.4 minutes, and a molar ratio of cobalt bromide to butane of 0.005:1.0.

TABLE I

| COMPOSITION OF THE LIQUID REACTION EFFLUENT FOR BUTANE OXIDATION | |
|---|---|
| Component | Weight % |
| Butane | 9.40 |
| Acetone | 0.123 |
| Methyl Acetate | 1.67 |
| Ethyl Acetate | 1.45 |
| Methyl Ethyl Ketone | 1.70 |
| s-Butyl Acetate | 0.479 |
| n-Butyl Acetate | 0.037 |
| Propionic Acid | 0.890 |
| Butyric Acid | 0.365 |
| 3-Br-2-Butanone | 0.726 |
| Unknowns | 1.03 |
| Water | 16.39 |
| Formic Acid | 0.318 |
| Acetic Acid | 61.54 |
| CO | 0.281 |
| $CO_2$ | 3.56 |
| $CH_4$ | 0.016 |
| $C_2H_6$ | 0.025 |
| Cobalt | 0.25 |

Portions of such liquid reaction effluent are subjected to decompression to gauge pressures of 2.6, 4.24, 6.0, 9.5 and 14.0 kg.cm$^2$ at temperatures which permit removal of at least 80 weight percent of the unreacted butane. The weight percent of each of the original components in the liquid reaction effluent are shown in TABLES II and III to follow:

TABLE II

DECOMPRESS LIQUID REACTION EFFLUENT
EFFECT OF TEMPERATURE AND PRESSURE

| Temperature, °C. | 119.4 | 122.8 | 124.8 | 128.4 | 135 | 138 |
|---|---|---|---|---|---|---|
| Pressure, kg/cm$^2$ | 2.6 | 2.6 | 2.6 | 2.6 | 4.24 | 4.24 |
| Amount Removed, wt. % | 14.8 | 16.8 | 18.2 | 21.8 | 14.7 | 18.1 |
| Component Removed wt. % | | | | | | |
| Acetic Acid | 5.2 | 6.7 | 7.8 | 10.8 | 5.4 | 8.0 |
| Water | 10.2 | 12.9 | 14.8 | 20.1 | 10.7 | 15.4 |
| Butane | 86.6 | 88.9 | 90.1 | 92.6 | 83.7 | 88.0 |
| Methyl Acetate | 30.6 | 36.0 | 39.3 | 47.4 | 29.4 | 37.6 |
| Ethyl Acetate | 24.1 | 29.0 | 32.0 | 39.8 | 23.5 | 31.1 |
| Formic Acid | 6.4 | 8.1 | 9.3 | 12.8 | 6.5 | 9.4 |
| Propionic Acid | 2.7 | 3.6 | 4.2 | 6.0 | 3.0 | 4.6 |
| Acetone | 25.9 | 30.8 | 33.8 | 41.6 | 24.7 | 32.3 |
| MEK | 18.1 | 22.1 | 24.7 | 31.5 | 17.7 | 24.0 |

TABLE III

DECOMPRESS LIQUID REACTION EFFLUENT
EFFECT OF TEMPERATURE AND PRESSURE

| Temperature, °C. | 144.7 | 147 | 161.8 | 176.9 | 176.7 | 148.9 |
|---|---|---|---|---|---|---|
| Pressure, kg/cm$^2$ | 6.0 | 6.0 | 6.0 | 9.5 | 14.0 | 14.0 |
| Amount Removed, wt. % | 14.0 | 15.3 | 32.1 | 26.7 | 15.0 | 10.9 |
| Component Removed wt. % | | | | | | |
| Acetic Acid | 5.1 | 6.0 | 20.8 | 16.0 | 4.3 | 6.6 |
| Water | 10.3 | 12.0 | 36.3 | 29.5 | 8.3 | 3.0 |
| Butane | 80.4 | 82.7 | 92.1 | 87.1 | 88.8 | 82.8 |
| Methyl Acetate | 26.8 | 29.9 | 60.7 | 50.8 | 14.1 | 3.9 |
| Ethyl Acetate | 21.6 | 24.4 | 54.2 | 44.8 | 14.4 | 4.6 |
| Formic Acid | 6.1 | 7.1 | 23.7 | 18.2 | — | 1.5 |
| Propionic Acid | 3.0 | 3.5 | 13.3 | 10.6 | 4.1 | 1.2 |
| Acetone | 22.4 | 25.2 | 54.9 | 45.0 | 14.1 | 4.2 |
| MEK | 16.2 | 18.5 | 45.5 | 36.6 | 13.1 | 4.4 |

The data in TABLE IV illustrates that the reaction effluent from the oxidation of liquid n-butane with oxygen gas in liquid acetic acid containing cobalt, manganese and bromine as components of catalysis is quite similar to the reaction effluent obtained from the same oxidation conducted in liquid acetic acid containing cobalt and bromine as components of catalysis as illustrated by TABLE I.

TABLE IV

OXIDATION OF n-BUTANE IN PRESENCE OF Co—Mn—Br CATALYST

Conditions:
Temperature 182° C.
Pressure 63.6 kg/cm$^2$ gauge
Residence time of 51 to 54 min.
Gram Atom Ratio of Co:Mn of 1:1
Gram Atom Ratio Br:Co + Mn of 2:1
Milligram Atom Metal:Gram Mole Butane 50:1.0
Mole Ratio O$_2$ to Butane of 78:1.0

Reaction Effluent Composition

| Component | Weight % |
|---|---|
| Butane | 0.14 to 0.27 |
| Acetone | N.D. |
| Methyl Acetate | 0.58 to 0.69 |
| Ethyl Acetate | 1.11 to 1.19 |
| Butyl Acetates | 0.37 to 0.61 |
| Propionic Acid | 3.51 to 5.09 |
| Butyric Acid | 0.52 to 0.69 |
| 3-Br-2-Butanone | 0.23 to 0.33 |
| Unknowns | 0.41 to 0.65 |
| Water | 18.0 to 18.8 |
| Formic Acid | 1.16 to 1.34 |

TABLE IV-continued
OXIDATION OF n-BUTANE IN PRESENCE OF Co—Mn—Br CATALYST

| Acetic Acid | 65.3 to 71.2 |
|---|---|

"N.D." is none detected.

The decompression-debutanization of liquid reaction effluent is followed by the thermal conversion of 3-bromo-2-butanone to MEK and inorganic bromide conducted at a temperature of from 150° C. up to 200° C., preferably at a temperature of from 170° C. up to 200° C. and at a gauge pressure of from 10 up to 30 kg/cm$^2$ for from 40 up to 150 minutes, preferably from 80 to 60 minutes. Under the preferred conditions of maintaining the decompressed and debutanized liquid reaction mixture at a temperature of from 170° C. up to 200° C. and at a gauge pressure of from 10 up to 30 kg/cm$^2$ for from 80 to 60 minutes (longer time at lower temperature and shorter time at higher temperature), substantially all of the 3-bromo-2-butanone will have been converted to MEK and inorganic bromide or bromides. For example, with an initial 3-bromo-2-butanone content of 0.35 to 0.80 weight percent in the decompressed-debutanized portion of the liquid reaction effluent, the preferred heat treatment of said portion converts its 3-bromo-2-butanone content to the range of from not detectable to 0.02 weight percent.

Such preferred heat treatment of the decompressed-debutanized liquid reaction mixture provides a feed for fractional distillation from which a low boiling organic (butane, acetone, methyl acetate, ethyl acetate, MEK, sec. butyl acetate and n-butyl acetate) fraction including acetic acid and water with a total bromine content of 3.5 to 4.5 weight percent and amounting to 7 to 10 wt.% of the feed can be removed and recycled to the n-butane oxidation. An acetic acid fraction amounting to 70 to 78 weight percent of the feed and containing 85 to 95 weight percent acetic acid, 0.5 to 5 weight percent water, 3-bromo-2-butanone of from 0 (not detectable) to 0.005 wt.% and a total bromide content of not more than 0.04 wt.%, and a residue or bottoms fraction amounting to 7 to 10 wt.% of the feed and containing from 49 to 85 wt.% acetic acid, from 0 to 0.5 wt.% water, from 1.4 to 2.8 wt.% catalyst metals, up to 8 wt.% total bromine, and up to 0.01 wt.% 3-bromo-2-butanone.

The distillation of the heat treated liquid to obtain a feed for the cryogenic concentration of acetic acid can be a simple distillation suitable to separate the water, acetic acid and associated organic materials from catalyst metal and inorganic bromides together with materials boiling higher than acetic acid as well as some acetic acid to leave a fluid residue fraction. However, it is preferred that the distillation be a continuous fractionation which, advantageously, can provide as a second (acetic acid) fraction one with a minimum amount of water by forming in the rectification zone an azeotropic mixture with the acetates and low boiling ketone impurities. The first fraction comprises water, some acetic acid and said acetates, and ketones which upon condensation form two immiscible liquid phases. The top phase is the acetate-ketone or organic phase and, of course, contains a small amount of acetic acid and water. The bottom phase is mainly a water phase with from 5 to 10 wt.% acetic acid. Together those two phases amount to from 5 to 25 weight percent of the feed to the fractionation. It is preferred to conduct the fractionation by charging the feed between the stripping and rectification zones, withdrawing a vapor acetic acid product below said feed entry, that is, withdrawing the vapor product or second fraction from the stripping zone so no catalyst metal or inorganic bromide contaminates the second fraction, to discard the organic phase portion of the first fraction or recycle it to the oxidation of n-butane, and to use the aqueous phase as reflux to the rectification zone. By such recycle of the aqueous phase portion of the first fraction there can be withdrawn from the stripping zone an acetic acid vapor fraction containing from 0.5 up to 8 weight percent water which can readily be concentrated to a "glacial" product by the cryogenic final step of this invention.

Suitable for such continuous fractionation is a column having trays or packing of 50 to 60% of theoretical separation efficiency. Such a column will have as its top rectification zone from 15 to 12 trays or packed units and as its stripping from 10 to 20 trays or packed units. The second or concentrated acetic acid fraction is withdrawn 10 trays or packed units below the feed entrance. Such a continuous fractionation is conducted at essentially atmospheric pressure at the top of the column with a bottom or reboiler temperature of from 120° C. up to 135° C. using a reflux ratio of from 20:1 to 30:1.

The acetic acid fraction removed from the heat treated decompressed-debutanized liquid reaction mixture is subjected to one or more sequences of continuous fractional crystallization by the technique which cools the fraction to freeze out an acetic acid-water eutectic crystalline magma having an acetic acid content higher than the acetic acid content of said fraction and leaves an acetic acid mother liquor having a water content higher than the water content of said fraction, moves said crystalline magma countercurrent to the flow of the mother liquor, melts at least a portion of the crystalline magma before its final composition is removed from the fractional crystallization system as product, and moves the melt liquor also countercurrent to the movement of the crystalline magma so that said flowing melt liquor and mother liquor wash the oppositely moving crystalline magma and mix to form a single waste liquor to be removed from the continuous crystallization system.

By the use of two or more of such continuous fractional crystallization systems in series flow relationship the origin acetic acid fraction can be processed to an anhydrous product from which the remaining $C_1$ to $C_4$ homologues of acetic acid can be separated by distillation.

The waste liquor from the foregoing continuous fractional crystallization system or from the first of two or more such systems is, according to the concept of the present invention, returned to the distillation step for concentration of its acetic acid content by removal of water. Such return can be to the still's boiler or after preheating to below, at or above the point of charging to the still column, the feed liquor which is the heat treated liquid portion of the butane oxidation effluent after its decompression and debutanization.

The conduct of two or more of the foregoing continuous fractional crystallization systems are carried out in the following manner. For two series connected systems, the waste liquor withdrawn from the second system is added as part of the feed to the first system and the lastly washed crystalline magma produced in the first system, and leaving it as a melt is fed to the second system. For the conduct of three or more systems, the waste liquor of the third system and melt of the lastly washed crystalline magma from the first system becomes the total feed to the second system, the melt of the lastly washed crystalline magma from the second system is the feed to the third system and the melt of the lastly washed crystalline magma from the third system becomes the product.

Three systems for effective continuous fractional crystallization are described by Gerard J. Arkenbout in CHEMTECH, vol. 6, September 1976, pages 596 to 599. Two of such systems comprise slow crystallization to maximize crystal purity and conveniently separable sized crystals followed by washing of the crystals formed by a melt of at least an outer portion of the last to form crystals in countercurrent flow with respect to crystal formation. One system effects such cooling and countercurrent washing by chilling the liquid feed in a long horizontal crystallizer whose inner surfaces, cooled by indirect heat exchange, are scraped by a helical screw end which advances the crystals as they begin to form near the feed end through to the discharge end. The resulting suspension of crystals in mother liquor discharges into the upper portion of a vertical column having a reciprocating piston periodically pushing down from the top of the column past the entry of the slurry into the column and forcing the slurry downward and then withdrawing toward the top of the column. The column also has, at the upper portion thereof a wall filter which extends from just below entry of the suspension down to slightly below the furthest downward thrust of the piston. The compression of the entering suspension by the piston forces mother liquor through the wall filter and compacts the crystals against the downwardly moving bed of previously compressed crystals. Near the bottom portion of the column a heating zone is provided to melt the compacted crystals reaching said heating zone. A valved liquid product exit is provided in the bottom of the column. The flow of liquid through the valve is adjusted so that the downwardly moving bed of compacted crystals forces only a part of the melt of the crystals out of the bottom of the column which forces upwardly the remaining portion of the melt of the crystals. The upwardly forced portion of the melt of crystals flows past the next upward adjacent portion of crystals before they move into the melting zone and displaces mother liquor from and/or melts the outer surfaces of the next upward adjacent portion of crystals, thus forming a new liquid in contact with them of lower impurity content which continues upward displacement of mother liquor from and/or melting outer layers of crystals contacted. As the bed of compressed crystals moves downward in contact with the upwardly moving liquid, new crystals form or crystals grow which have a lower impurity content.

The second system containing the scraped wall surface chilling zone and vertical washing column has a long horizontal freezing zone made up of a series of chilled, scraped inner surface crystallization zones cooled by indirect heat exchange with a cold liquid. Each crystallization zone has not only scrapers to remove crystals from the cold inner surfaces but also has means for pumping least pure melt in the direction of the mother liquor discharge. The feed enters near the center of the last crystallization zone and the mother liquor is forced out one end of said zone. A temperature gradient is imposed on each of the crystallization zones such that a countercurrent flow of melt and crystals is established. Crystals formed in the coldest portion of the last crystallization zone are forced into the preceding zone and are first partially melted, the melt returning to the last crystallization zone and the unmelted crystals in contact with melt of purer crystals grow on the chilled surface and are forced further in the direction of the washing column. The crystals of increasing purity are forced into and downwardly through the column in contact with rising melt formed at the bottom of the column in its heated portion and rising through the column of the downwardly moving crystals and thence into the first section of the series of crystallization zones. In this system crystals are grown from a melt as pure as possible rather than from the least pure rejected waste.

In neither of the two foregoing systems does recrystallization contribute to product purification. Consequently the separation power of those two separation systems is rather limited.

The third system is a continuous purification accomplished not only by crystallization and countercurrent washing of crystals but also by repeated continuous recrystallizations accomplished in quite an unusual manner. The recrystallizations are not conducted by redissolving each crystal crop in an extraneous solvent. Rather the recrystallizations are accomplished by several steps of grinding crystals during their travel down through the wash column toward its bottom heating zone which melts the final crystals. Such grinding steps result in high separation efficiency per unit height of the wash column. The comminuting of the large crystals results in small particles which are not stable and dissolve in the upwardly moving surrounding liquid. The continuous comminuting of crystals and the travel of particles by countercurrent flow of melt liquor to a new pure liquid phase and recrystallization from such purer liquid phase ultimately results in the growth of larger purer crystals through the imposition of concentration differences, analogous to those of distillation or extraction.

Such grinding can be accomplished by a plurality of ball mills set at various levels in the wash column, for example, steel or ceramic balls on perforated trays or sieve discs with vibration of the balls and/or the trays or discs.

Such a system comprises a cooled and scraped surface crystallizer mounted in a vertical position at the top of a washing column having a plurality of perforated trays or sieve discs (e.g., 5 to 40 per meter of column height), a bottom heating zone to melt the last formed crystals washed with rising melt, a bottom discharge for liquid purified product, a feed inlet below the top, several (e.g., 2 to 4) trays or discs, and an upper outlet above the top disc or tray but below the crystallizer for discharge of impurity enriched liquor. An example of the number and size of the balls for the needed comminuting are 30 balls of 12 mm diameter per 80 mm diameter sieve disc having openings of $0.6 \times 0.6$ mm.

The temperatures suitable for fractional crystallization of the acetic acid distillative fractions, compositions according to this invention, are governed by the freezing temperatures of their acetic acid-water contents. Such temperatures, for example, are known from tables of the freezing temperatures of acetic acid-water compositions, for example, those at pages 359 to 360 of volume 4 of the Physico-Chemical Constants of Binary Systems in Concentrated Solutions by Jean Timmermans, Interscience Publishers, Inc., New York (1960).

The following is provided to illustrate our presently contemplated best mode of conduct of the present invention so that those skilled in this art can readily practice our invention. However, as those skilled persons will appreciate, equivalent results can be obtained by selecting different operating conditions for each step from among the preferred operating conditions therefore suited to the needs of such persons as indicated by the compositions of each mixture to be processed. Thus the illustrative example of least mode of operation is not intended to impose any limitation on the conditions for the practice of the present invention, for such limitations are only imposed by the terms and conditions set out in the appended claims.

EXAMPLE

The impure acetic acid for use in this example is obtained by the continuous oxidation of liquid commercial n-butane (95% n-butane) with oxygen gas at a temperature of 193° C. and a gauge pressure of 77.3 kg/cm$^2$ in the presence of cobalt added as cobalt acetate tetrahydrate, and bromine added as hydrogen bromic acid (48% HBr). The continuously removed total liquid reaction effluent is decompressed to a gauge pressure of 28 kg/cm$^2$ and a temperature of 193° C. by venting unreacted n-butane together with oxides of carbon, methane, ethane, ethylene, propane, and butane. Such vented gases contain 60 to 65 weight percent n-butane, 30 to 35 weight percent oxides of carbon (mainly carbon dioxide and rather small amounts of the other named organic compounds). Said decompressed-debutanized liquid, hereafter designated "starting material," is heat treated at a temperature of 193° C. and 28 kg/cm$^2$ gauge pressure continuously at a residence time of ninety minutes.

The resulting liquid (hereafter "heat treated") is cooled to 105° C. and at that temperature is continuously fed, at the rate of 12.6 grams per minute to a distribution tray of a fractionation column comprising an upper rectification zone above the distribution tray, and below said tray, a stripping zone and a reboiler. The stripping zone is 50.8 mm internal diameter and has 10 trays functioning at 55 to 60% separation efficiency (i.e., 55 to 60% of a theoretical tray) between the distribution tray and the product vapor draw-off and 10 more trays in a 76.2 mm internal diameter column. The rectification zone is 50.8 mm in diameter and has 15 trays of 50 to 55% separation efficiency. The fractionation system is operated at one atmosphere (0 kg/cm$^2$ gauge) pressure, a reboiler temperature of 125° C. and a temperature of 105° C. at the top of the column. Concentrated acetic acid is withdrawn as a vapor from above the tenth tray below the distribution tray. The 105° C. temperature vapor at the top of the column is removed, cooled to condense the vapors to liquid and the resulting liquid condensate is collected in a settling tank from which the organic (top) phase and the aqueous (bottom) phase can be separately withdrawn. In this example the aqueous phase is used as reflux to the rectification zone and at equilibrium steady flow operation the reflux ratio is 20.4:1 with a reflux rate of 17.95 grams per minute.

The organic phase at 0.88 gram per minute (6.98% of the starting material) and the withdrawn reboiler liquid at 1.5 grams (11.9%) per minute are recycled to the butane oxidation. The concentrated acetic acid vapor (98.13 wt.% acetic acid and 0.5 wt.% water) is withdrawn at 8.1 grams (64.3% of the starting material) per minute, cooled to condense the vapor to liquid as feed for the cryogenic step for further concentrating the acetic acid to a water-free product. The aqueous phase (about 17.86 of the starting material) not recycled to the fractionation contains 18.8 weight percent acetic acid and 58.9 weight percent water.

TABLE V to follow provides the compositions of the materials acted upon and produced from the decompression step through the fractionation. Under the heading "Components," "MEK" is used to designate 2-butanone, both for the unsubstituted ketone and the 3-bromo-substituted ketone (e.g., 3-Br-MEK); and "$C_4$" is used to designate a butyl group (e.g., "Sec.-$C_4$" for the secondary butyl group and "n-$C_4$" as the normal butyl group).

TABLE V
DECOMPRESSION THROUGH FRACTIONATION

| Component, Weight Percent | Starting Material | Heat Treated |
|---|---|---|
| Butane | 0.02 | 0.02 |
| Acetone | 0.46 | 0.46 |
| Methyl Acetate | 1.80 | 1.80 |
| Ethyl Acetate | 1.16 | 1.16 |
| MEK | 1.69 | 2.015 |
| Sec-$C_4$ Acetate | 0.29 | 0.29 |
| n-$C_4$ Acetate | 0.05 | 0.05 |
| 3-Br—MEK | 0.69 | 0 |
| Formic Acid | 0.12 | 0.12 |
| Water | 23.62 | 23.62 |
| Acetic Acid | 65.43 | 65.43 |
| Propionic Acid | 2.38 | 2.38 |
| n-Butyric Acid | 0.91 | 0.91 |
| Unknowns | 0.95 | 0.95 |
| Ionic Bromine | 0.18 | 0.548 |
| Cobalt | 0.25 | 0.25 |

TABLE V
DECOMPRESSION THROUGH FRACTIONATION

| Component, Weight Percent | Fractions First Organic | $H_2O$ | 2nd | 3rd |
|---|---|---|---|---|
| Butane | 0.46 | 0 | 0 | 0 |
| Acetone | 2.94 | 1.45 | 0 | 0 |
| Methyl Acetate | 17.66 | 5.90 | 0 | 0 |
| Ethyl Acetate | 15.62 | 4.15 | 0 | 0 |
| MEK | 19.43 | 6.18 | 0 | 0 |
| Sec-$C_4$ Acetate | 5.59 | 0.96 | 0 | 0 |
| n-$C_4$ Acetate | 0.89 | 0.17 | 0 | 0 |
| 3-Br—MEK | 0 | 0 | 0 | 0 |
| Formic Acid | 0.49 | 0.31 | 0.29 | 0.25 |
| Water | 11.77 | 58.9 | 0.50 | 0.39 |
| Acetic Acid | 13.87 | 18.79 | 98.13 | 84.49 |
| Propionic Acid | 1.13 | 0.48 | 0.98 | 6.07 |
| n-Butyric Acid | 0.64 | 0.17 | 0.09 | 3.09 |
| Unknowns | 3.21 | 0.99 | 0 | 3.12 |
| Ionic Bromine | 0 | 0 | 0 | 4.48 |
| Cobalt | 0.01 | 0.01 | 0 | 1.40 |

The foregoing second fraction (condensed concentrated acetic acid vapor stream with only 0.5 wt.% water) is charged as feed to a combination of indirectly cooled horizontal tubular cyrstallizer closed at one end and at the other end joined to the top of a vertical cylindrical column in fluid flow relationship. Said column has a closed bottom so that the combination of tube and column comprises a closed, fluid retaining system. Said horizontal tube having an inner helical ribbon screw driven at one end of the helical screw and pivotally supported at each end of the tube, to its discharge end and to scrape material frozen to the inner wall of the tube; a feed inlet 75 to 85% of the length of the tube away from its closed end and a waste liquid outlet near said closed end; and an inlet to the jacket around said tube near the closed end thereof and an outlet from said jacket near the junction of said tube and column; means for supplying a flow of chilled coolant to the inlet of the jacket, withdrawing warmed coolant from the outlet of the jacket and extracting heat by indirect heat exchange from the circulating coolant to chill it for its return to the jacket's inlet; a crystalline product melter near the bottom closed end of the column. The helical ribbon screw-scraper can be driven at a rate of from 0.5 up to 2 revolutions per minute.

Said second fraction is precooled to a temperature of 18° C. and fed to the foregoing apparatus chilled by a solution of 50:50 water and ethylene glycol cooled by indirect heat exchange with a refrigerant to a temperature of −35° C. Said solution enters the jacket of the horizontal tubular crystallizer near the closed end of the horizontal tube. The ribbon screw-scraper is operated at 0.7 to 0.8 rpm. The heater at the bottom of the washing column is operated to provide a melt at a temperature between 16° C. and 17° C. The temperature of the crystallizer at its feed inlet is between −20° C. and −30° C. The melted product contains no water. The waste liquor contains 75 to 80 weight percent water and is recycled to the feed distribution tray of the fractionation column as part of the feed thereto for concentration.

What is claimed is:

1. The method of preparing an acetic acid product from the liquid reaction effluent obtained from the oxidation of liquid n-butane with oxygen gas at a temperature of from 120° C. up to 235° C. and a gauge pressure from 35 up to 210 kg/cm² in the presence of an acetic acid solution of the system of catalysis comprising bromide ions in combination with ions of cobalt or cobalt and manganese which liquid effluent in addition to the contaminants comprising unreacted butane esters and ketones boiling lower than acetic acid; formic propionic acid and butyric acid as well as catalyst metal salts; and oxides of carbon, methane and ethane; also contains 3-bromo-2-butanone as a contaminant; which method comprises decompressing such liquid reaction effluent to a gauge pressure of from 28 down to 0 kg/cm² to remove unreacted n-butane and coproduct gases; heating the decompressed liquid to and maintaining said liquid at a temperature of from 150° C. for at least 40 minutes up to a temperature of 200° C. for at least 40 minutes whereat 3-bromo-2-butanone is converted to 1-butene-3-one and one or more inorganic bromides; distilling such heat treated decompressed liquid to remove (a) water and organic materials boiling at a temperature below acetic acid as a first fraction, a second fraction comprising an acetic acid-water fraction containing formic, propionic and butyric acid and 3-bromo-2-butanone not converted to 1-butene-3-one and leaving a third or residue fraction containing inorganic bromides mainly as catalyst metal salts together with other high boiling materials dissolved in acetic acid and liquid at a temperature of from 116° to 150° C.; and subjecting the second distillation fraction to one or more steps of continuous fractional crystallization wherein the crystalline magma formed is washed by countercurrent flow of acetic acid mother liquor, and withdrawing therefrom as product acetic acid, the melt of the last washed crystals.

2. The method of claim 1 wherein the step of distilling the heat-treated and decompressed liquid is accomplished through fractional distillation in a system comprising a rectification zone, a stripping zone and a feed inlet between said zones by introducing said heat-treated and decompressed liquid into said feed inlet, withdrawing from the rectification zone the first fraction as a liquid and permitting it to settle into an organic phase and an immiscible aqueous phase, recycling the aqueous phase as reflux to the rectification zone and withdrawing the acetic acid-water second fraction as a vapor product from the stripping zone.

3. The method of claim 2 wherein the aqueous acetic acid washed crystalline magma also washed with a partial melt of a prior formed crystalline magma, the second to form crystalline magma is washed with a melt of washed first formed crystalline magma and such melt washes flow countercurrent to the movement of the crystalline magmas formed and comingles and mixes with the mother liquor formed from the feed so that as the crystalline magmas advance to be melted and discharge as product they are progressively in contact with a liquor of higher purity acetic acid than the mother liquor from which the crystalline magma separated.

* * * * *

UNITED STATES PATENT OFFICE
CERTIFICATE OF CORRECTION

Patent No. 4,278,503  Dated July 14, 1981

Inventor(s) Martin A. Zeitlin and Jon J. Harper

It is certified that error appears in the above-identified patent and that said Letters Patent are hereby corrected as shown below:

Patent reads

| Col. | Line | | |
|---|---|---|---|
| 2 | 47 | "hydrogeation" should be | --hydrogenation-- |
| Abstract | 8 | "bromo-ketone" should be | --bromoketone-- |
| 4 | 37 | "kg. $cm^2$," should be | --$kg/cm^2$,-- |
| 4 | 64 | "kg. $cm^2$" should be | --$kg/cm^2$-- |
| 4 | 67 | "are shown" should be | --is shown-- |
| 7 | 62 | "are carried" should be | --is carried-- |
| 13 | 9 | "acidwater" should be | --acid-water-- |
| 14 | 4 | "comingles" should be | --commingles-- |

Signed and Sealed this

Twenty-fourth Day of November 1981

[SEAL]

Attest:

GERALD J. MOSSINGHOFF

Attesting Officer   Commissioner of Patents and Trademarks